United States Patent [19]

Kohn et al.

[11] Patent Number: 4,483,992

[45] Date of Patent: Nov. 20, 1984

[54] ALKYLTHIO SUBSTITUTED PHENOXY ALKANOIC ACID ESTERS

[75] Inventors: Gustave K. Kohn, Palo Alto; Joe T. Bamberg, Redwood City, both of Calif.

[73] Assignee: Zoecon Corporation, Palo Alto, Calif.

[21] Appl. No.: 406,791

[22] Filed: Aug. 10, 1982

Related U.S. Application Data

[63] Continuation-in-part of Ser. No. 405,853, Aug. 6, 1982.

[51] Int. Cl.³ .................... C07D 213/64; A01N 43/40
[52] U.S. Cl. .................................. 546/302; 546/157; 544/345; 548/166; 548/221; 560/11; 560/12
[58] Field of Search .......................................... 546/302

[56] References Cited

U.S. PATENT DOCUMENTS

| | | | |
|---|---|---|---|
| 3,379,752 | 4/1968 | Bolhofer | 560/53 |
| 4,134,751 | 1/1979 | Nishiyama | 71/94 |
| 4,216,007 | 8/1980 | Nishiyama | 71/94 |
| 4,348,221 | 9/1982 | Szczepanski | 71/94 |

*Primary Examiner*—Alan L. Rotman
*Attorney, Agent, or Firm*—Jacqueline S. Larson; Hana Dolezalova; Donald W. Erickson

[57] ABSTRACT

3-Alkylthio (arylthio)-4-substituted phenoxy alkanoic acid esters, derivatives thereof, and the use thereof for the control of weeds.

7 Claims, No Drawings

ALKYLTHIO SUBSTITUTED PHENOXY ALKANOIC ACID ESTERS

This invention relates to novel 3-alkylthio (arylthio)-4-substituted phenoxy alkanoic acid esters, derivatives thereof, and the use thereof for the control of weeds.

The novel compounds of the present invention are represented by the following formula (A):

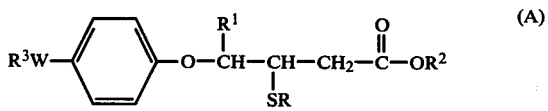

wherein,
R is hydrogen, lower alkyl or aryl;
R¹ is hydrogen or lower alkyl;
R² is lower alkyl, lower alkenyl or lower alkynyl;
W is oxygen, sulfur or amino; and
R³ is one of the groups

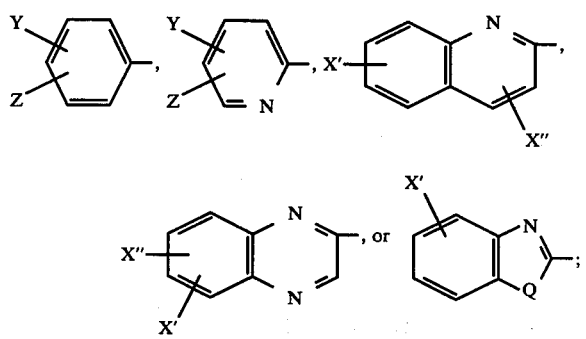

in which,
each of Y and Z is independently selected from hydrogen, lower alkyl, lower haloalkyl, lower alkoxy, lower haloalkoxy, bromo, chloro, fluoro, nitro and cyano;
each of X' and X" is independently selected from hydrogen, fluoro, chloro, bromo, trifluoromethyl, methoxy or nitro, provided that both X' and X" cannot be trifluoromethyl, methoxy or nitro; and
Q is oxygen or sulfur; and
the

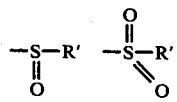

derivatives thereof at C-3 position wherein R' is lower alkyl or aryl.

In the description and claims hereinafter, each of R-R³, Q, W, X', X", Y and Z is as defined above, unless otherwise specified.

The compounds of formula (A) wherein R is lower alkyl or aryl can be synthesized by the reaction of a mercaptide with a mesylate of formula (I) in an organic solvent, such as hexane, benzene, dimethylformamide and the like, inert to the reaction. The compounds of formula (A) wherein R is hydrogen can be synthesized by reaction of a compound of formula (I) with alkali hydrosulfide such as sodium hydrosulfide in an organic solvent inert to the reaction.

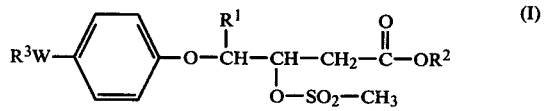

The mesylates of formula (I) are prepared by the reaction of mesyl chloride with the corresponding 3-hydroxy compound. The corresponding 3-hydroxy compounds can be prepared by methods described in U.S. Pat. No. 4,408,076.

The

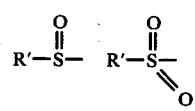

compounds of formula (A) are prepared by oxidation of the corresponding thioether using, e.g., m-chloroperbenzoic acid and the like.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to three halogen atoms.

The term "lower alkoxy" refers to an alkoxy group, straight or branched, having a chain length of one to eight carbon atoms. The term "lower haloalkoxy" refers to a lower alkoxy group substituted with one to three halogen atoms.

The term "aryl" refers to phenyl and a substituted phenyl group such as p-methylphenyl and p-chlorophenyl.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

While some of the compounds of the present invention have activity on broad leaf plants, the compounds, in general, demonstrate a higher level of herbicidal activity on the grass weeds. Grass plant (weed) species on which the compounds of the present invention show effective herbicidal activity include shattercane, crabgrass, sprangletop, wild oats, bermudagrass, tall fescue, rice, wheat, barley, corn, blue panicum, foxtails, rough bluegrass, winter rye, annual ryegrass, watergrass and Johnsongrass. It appears to be most effective to apply the active compound prior to the heading stage of the grass weed.

Methods of preparing herbicidal formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

The compounds of the present invention, in view of their broadspectrum grass weed herbicidal activity, can be advantageously combined with broadleaf weed herbicides for broadspectrum postemergence weed control in most broadleaf crops. Examples of herbicides which can be combined with a compound of the present invention include glyphosate, bentazone, diuron, paraquat, 2,4-D, 2,4-DB, diquat, endothal, dinoseb, dicamba, norflurazon, nitrofen, cyanozine, methazole, mefluidide, metribuzin, cycloate, fluometuron, linuron, dalapon, bifenox and alachlor for controlling a broad spectrum of weeds.

The term "herbicide," as used herein, refers to an active ingredient which modifies the growth of plants because of phytotoxic or plant growth regulating properties so as to retard the growth of the plant or damage the plant sufficiently to kill it.

The following examples are provided to illustrate the practice of the present invention. Temperature is given in degrees Centigrade. "RT" means room temperature.

EXAMPLE 1

Into a three neck flask, purged with nitrogen, cooled in an ice water bath, containing ethyl 4-[4-(4-trifluoromethylphenoxy)phenoxy]-3-hydroxypentanoate (2.05 g) in 20 ml of hexane/benzene (1:1) is added slowly mesyl chloride (0.65 g, 1.1 equiv.) in 10 ml of hexane/benzene (1:1) and trimethylamine (0.67 g, 1.3 equiv) in 10 ml of hexane/benzene (1:1) at 0°. The reaction mixture is stirred for about one hour. Then the mixture is worked up by addition of methylene chloride and dilute acetic acid and partitioning with ice water. The organic phase is dried over magnesium sulfate, filtered and evaporated under vacuum to yield ethyl 4-[4-(4-trifluoromethylphenoxy)phenoxy]-3-methanesulfonyloxypentanoate, an oil, which can be purified by column chromatography, silica gel, eluting with hexane/ethyl acetate (4:1).

Fifty percent NaH oil dispersion (0.384 g) is washed with benzene/hexane (1:1), then benzene/hexane (30 ml) added and methyl mercaptan bubbled in to saturation. Solvent is removed by syringe and dimethylformamide (25 ml) added. To a solution of about 1.0 equiv of ethyl 4-[4-(4-trifluoromethylphenoxy)phenoxy]-3-methanesulfonyloxypentanoate in benzene is added, slowly, the foregoing mercaptide with agitation and cooling. After addition is complete, agitation is continued for about one hour. The reaction is worked up by washing with ice water and dilute acetic acid and CH$_2$Cl$_2$, dilute KHCO$_3$, and water and CH$_2$Cl$_2$, collecting the CH$_2$CL$_2$ phases, drying over MgSO$_4$ and concentrating under vacuum. The concentrate is purified by prep. thin layer chromatography developing with 83% hexane and 17% ethyl acetate to give ethyl 4-[4-(4-trifluoromethylphenoxy)phenoxy]-3-methylthio pentanoate (II; R is methyl, R$^2$ is ethyl, R$^3$ is 4-trifluoromethylphenyl). I.R. (neat) r=1730(C═O)cm$^{-1}$.

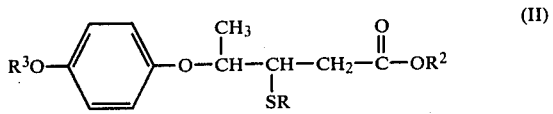
(II)

The process of this example is repeated using the 3-mesylate of the compound under Table 1 to yield the corresponding 3-mesylate.

TABLE 1

1. Ethyl 4-[4-(5-trifluoromethyl-2-pyridyloxy)phenoxy]-3-hydroxypentanoate.
2. Ethyl 4-[4-(3-chloro-5-trifluoromethyl-2-pyridyloxy)phenoxy]-3-hydroxypentanoate.
3. Ethyl 4-[4-(3,5-dichloro-2-pyridyloxy)-phenoxy]-3-hydroxypentanoate.
4. Methyl 4-[4-(2-chloro-4-trifluoromethylphenoxy)-phenoxy]-3-hydroxypentanoate.
5. Ethyl 4-[4-(2,4-dichlorophenoxy)phenoxy]-3-hydroxypentanoate.

EXAMPLE 2

Following the procedure of Example 1, sodium ethyl mercaptide is reacted with ethyl 4-[4-(3-chloro-5-trifluoromethyl-2-pyridyloxy)phenoxy]-3-methanesulfonyloxypentanoate to yield the corresponding -3-ethylthio compound (II; R is ethyl, R$^2$ is ethyl, R$^3$ is 3-chloro-5-trifluoromethyl-2-pyridyl).

EXAMPLE 3

A mixture of ethyl 4-[4-(3-chloro-5-trifluoromethyl-2-pyridyloxy)phenoxy]-3-methanesulfonyloxypentanoate and sodium hydrosulfide (1.5 equiv.) in ethanol is reacted at R.T. overnight. The reaction mixture is worked up as in Example 1 to yield the 3-thiol (II; R is hydrogen, R$^2$ is ethyl, R$^3$ is 3-chloro-5-trifluoromethyl-2-pyridyl).

What is claimed is:

1. A compound of the following formula (A):

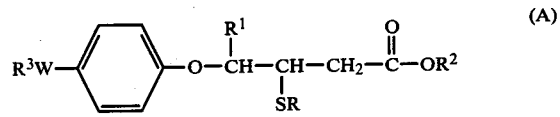
(A)

wherein,
R is hydrogen or lower alkyl;
R$^1$ is hydrogen or lower alkyl;
R$^2$ is lower alkyl, lower alkenyl or lower alkynyl;
W is oxygen; and
R$^3$ is

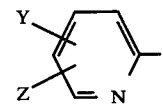

in which,
each of Y and Z is independently selected from hydrogen, lower haloalkyl, bromo, chloro and fluoro.

2. A compound of the following formula according to claim 1:

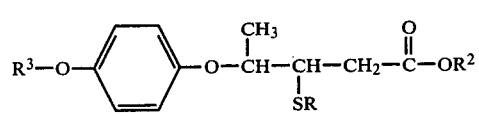

wherein
R is hydrogen or lower alkyl and R$^2$ is lower alkyl.

3. A compound according to claim 2 wherein R$^3$ is

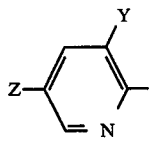

in which Y is hydrogen or chloro and Z is chloro or trifluoromethyl.

4. A compound according to claim 3 wherein Y is chloro and R is methyl.

5. A compound according to claim 3 wherein Y is chloro, Z is trifluoromethyl and R is methyl.

6. A compound according to claim 3 wherein Y is hydrogen, Z is trifluoromethyl and R is methyl.

7. A compound according to claim 2 wherein R is hydrogen, $R^2$ is lower alkyl, and $R^3$ is the group

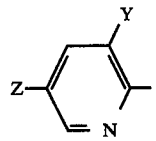

wherein Y is hydrogen or chloro and Z is chloro or trifluoromethyl.

* * * * *